United States Patent
Kurrus et al.

(10) Patent No.: US 8,518,013 B2
(45) Date of Patent: Aug. 27, 2013

(54) MULTI-LUMEN CATHETER WITH INCREASED FLOW AREA

(75) Inventors: Michael R. Kurrus, Ellettsville, IN (US); Brian Feng, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/497,064

(22) PCT Filed: Sep. 24, 2010

(86) PCT No.: PCT/US2010/050189
§ 371 (c)(1),
(2), (4) Date: Mar. 20, 2012

(87) PCT Pub. No.: WO2011/038223
PCT Pub. Date: Mar. 31, 2011

(65) Prior Publication Data
US 2012/0179103 A1    Jul. 12, 2012

Related U.S. Application Data

(60) Provisional application No. 61/245,380, filed on Sep. 24, 2009.

(51) Int. Cl.
*A61M 25/00*    (2006.01)
(52) U.S. Cl.
USPC .................................................... 604/523
(58) Field of Classification Search
USPC .................... 604/43, 164.01, 164.1
See application file for complete search history.

(56) References Cited

U.S. PATENT DOCUMENTS

| | | | |
|---|---|---|---|
| 4,894,057 A * | 1/1990 | Howes | 604/523 |
| 5,188,593 A * | 2/1993 | Martin | 604/43 |
| 5,515,851 A | 5/1996 | Goldstein | |
| 5,695,479 A * | 12/1997 | Jagpal | 604/264 |
| 6,827,710 B1 | 12/2004 | Mooney et al. | |
| 6,921,396 B1 | 7/2005 | Wilson et al. | |
| 2001/0027819 A1 | 10/2001 | Wages et al. | |
| 2006/0074400 A1* | 4/2006 | Carrillo et al. | 604/523 |
| 2007/0049960 A1 | 3/2007 | Stephens et al. | |
| 2009/0054874 A1* | 2/2009 | Barron et al. | 604/524 |

FOREIGN PATENT DOCUMENTS

| WO | WO 2005/099807 | 10/2005 |
|---|---|---|
| WO | WO 2007/078753 | 7/2007 |

* cited by examiner

*Primary Examiner* — Aarti B Berdichevsky
(74) *Attorney, Agent, or Firm* — Brinks Hofer Gilson & Lione (57) ABSTRACT

In at least one embodiment, a catheter for insertion into a patient for providing treatment is provided. The catheter comprises an elongated shaft having a proximal portion extending to a distal portion. The proximal portion has a plurality of first lumens formed therethrough and at least one septum separating the first lumens in non-coaxial relationship with each other. The first lumens each have an associated flow area for providing the treatment through the proximal portion. The distal portion has a second lumen in fluid communication with the first lumens. The septum terminates distally in the proximal portion to merge the first lumens with the second lumen. The second lumen has a second flow area that is greater than any one of the associated flow areas of the first lumens for providing the treatment to the patient.

15 Claims, 7 Drawing Sheets

MULTI-LUMEN CATHETER WITH INCREASED FLOW AREA

CROSS-REFERENCE TO RELATED APPLICATIONS

This application is related to and claims the benefit of priority to PCT/US2010/050189, filed Sep. 24, 2010, which application claims priority to U.S. Provisional Patent Application Ser. No. 61/245,380, filed Sep. 24, 2009, entitled "MULTI-LUMEN CATHETER WITH INCREASED FLOW AREA," both of which are incorporated herein by reference in their entirety.

BACKGROUND OF THE INVENTION

1. Field of the Invention

The present invention relates generally to catheters and more particularly, to a multi-lumen catheter with an increased flow area (e.g. increased cross-sectional area of the lumen/s for increasing the flow rate capabilities of the catheter) and a method for making the multi-lumen catheter.

2. Background of the Invention

Catheters for the introduction or removal of fluids may be positioned in various venous locations and cavities throughout the body of a patient for introduction of fluids to the body or removal of fluids from the body. Such catheterizations are often performed using a catheter with multiple lumens. Examples of such catheters are central venous catheters which are typically used for medical procedures such as blood pressure monitoring, blood sampling and the administration of drugs, diagnostic materials and fluids to a patient. These procedures often require that the catheter have sufficiently sized lumens for providing therapeutic and/or diagnostic treatments, such as for example, administering fluids to the patient or withdrawing/removing fluid (e.g. body fluids or otherwise) from the patient.

Generally, a central venous catheter is surgically inserted into a vein, such as the basilica, cephalic, subclavian, or jugular, with the distal tip of the catheter residing in the superior vena cava. These catheters are typically introduced using percutaneous entry techniques, such as the well-known Seldinger technique. In the Seldinger technique, the physician makes an oblique entry into the vein with a beveled needle. A wire guide is then inserted through the bore of the needle about 5 to 10 centimeters into the vein. The needle is thereafter withdrawn, leaving the wire guide in place. The catheter is then inserted over the wire guide, and advanced through the skin at the needle puncture site and into the vein. The Seldinger technique can be modified to include a peelable introducer which can be used to dilate the body vessel. In particular, the introducer sheath can be placed over the wire guide, and after removal of a dilator, the catheter can be placed through the sheath for insertion into the patient. In either of these procedures, the catheter is preferably sized such that the outer diameter (e.g. relatively small outer diameter) facilitates introduction of the catheter through the skin and into the vein without occluding the vein. Once the catheter is in place within the vein, the wire guide is withdrawn and therapeutic treatment using the catheter can begin. Preferably, the catheter has sufficient flow area (e.g. relatively large flow area) for each of its lumens for providing various treatments to the patient, such as for example, during infusion therapy. At the conclusion of the therapeutic treatment, the catheter is withdrawn from the patient. Preferably, the outer diameter of the catheter is configured (e.g. relatively small outer diameter) to facilitate the catheter being withdrawn from the patient. Currently available multi-lumen catheters with relatively large inner diameter lumens and currently available multi-lumen catheters with relatively small outer diameter shafts result in two diametrically opposed multi-lumen catheter constructions. That is, multi-lumen catheters with relatively large inner diameter lumens have corresponding relatively large outer diameter shafts and multi-lumen catheters with relatively small outer diameter shafts have corresponding relatively small inner diameter lumens.

Accordingly, it may be desirable to have a multi-lumen catheter with increased flow area for providing treatment to a patient while having a relative small outer diameter for facilitating insertion into and/or withdrawal from the patient.

BRIEF SUMMARY OF THE INVENTION

In satisfying the above need and overcoming the above and other drawbacks and limitations of the known technology, the present invention provides a catheter for insertion into a patient's body for providing treatment to the patient. The catheter comprises an elongated shaft having a proximal portion extending to a distal portion. A plurality of first lumens (e.g. proximal lumens) is formed through the proximal portion and at least one septum separates the first lumens in non-coaxial relationship with each other. The first lumens each have an associated flow area for providing the treatment through the proximal portion. The distal portion has a second lumen (e.g. distal lumen) in fluid communication with the first lumens. The septum terminates distally in the proximal portion to merge the first lumens with the second lumen. The second lumen has a second flow area that is greater than any one of the associated flow areas of the first lumens for providing the treatment to the patient.

In at least one other embodiment of the present invention, a catheterization kit is provided. The kit comprises the catheter as discussed in the foregoing paragraph and a wire guide for providing the catheter a path during insertion into the patient's body. A needle is provided for introducing the wire guide into the patient's body.

In one example, a method of making a catheter for insertion into a patient's body for providing treatment to the patient is provided. The method comprises forming a plurality of first lumens through a proximal portion of a catheter including forming at least one septum separating the first lumens in non-coaxial relationship with each other. The first lumens each have an associated flow area for providing the treatment through the proximal portion. A second lumen is formed through a distal portion of the catheter and the septum is terminated distally in the proximal portion of the catheter to merge the first lumens with the second lumen. The second lumen has a second flow area that is greater than any one of the associated flow areas of the first lumens for providing the treatment to the patient.

Further objects, features, and advantages of the invention will become apparent from consideration of the following description and the appended claims when taken in connection with the accompanied drawings.

DETAILED DESCRIPTION OF THE INVENTION

Detailed embodiments of the present invention are disclosed herein. It is understood however that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis for the claims and for teaching one skilled in the art to practice the present invention.

The present invention seeks to overcome some of the problems associated with introducing a catheter into a patient and removing the catheter from the patient while providing sufficient volumetric flow of therapeutic or diagnostic materials to or from the patient. Preferably, the present invention provides a multi-lumen catheter and a method for making the catheter which facilitates introducing the catheter to the patient and/or removing the catheter therefrom while providing a sufficiently sized multi-lumen arrangement for providing therapeutic and/or diagnostic treatment to the patient (e.g. administering and/or withdrawing fluids).

The present invention employs a catheter having a plurality of smaller lumens formed through its proximal portion and at least one septum separating each of the smaller lumens. The septum terminates distally in the proximal portion to merge the smaller lumens into a single larger distal lumen. The flow area of the larger distal lumen is greater than any one of the associated flow areas of the smaller lumens, and is preferably greater than the combined flow area of the smaller lumens by at least about the cross-sectional area of the terminated septum. In at least one embodiment, the outer diameter of the distal portion is substantially the same as the outer diameter of the proximal portion, despite the greater flow area of the larger distal lumen, to facilitate introducing and/or removing the catheter from the patients' body.

In one example, applicants have found that even a slightly greater flow area for the single larger distal lumen relative to the effective combined flow areas of the smaller lumens, e.g., flow area of the single larger distal lumen greater than the effective combined flow areas of the smaller lumens by at least the cross-sectional area of the septum, can significantly increase the volumetric flow rate through the catheter. For instance, fluid flow through a circular cross-sectional flow area ($A=\pi r^2$) of a catheter shaft can be described by Poiseuille's Law which is $\Delta P=(8\mu LQ)/(\pi r^4)$, where $\Delta P$ is the pressure drop, L is the length of the catheter shaft, $\mu$ is the dynamic viscosity, Q is the volumetric flow rate, r is the radius of the lumen of the catheter shaft which is equal to half its diameter ($r=\frac{1}{2}D$), and $\pi$ is approximately 3.14. Since the radius (r) is to the fourth power, approximately a 0.005 inch increase (e.g. assuming septum to be 0.005 inch thick) in the diameter of about a 0.030 inch diameter lumen (e.g. assuming effective combined diameter of smaller lumens is about 0.030 inch) at a dynamic viscosity ($\mu$) of about 6.8 centipoise (cP) through approximately a 50 centimeter (cm) long catheter shaft (e.g. assume the septum terminates distally in the proximal portion within a nominal distance) at a pressure drop ($\Delta P$) of about 25 pounds per square inch (psi) almost doubles the flow rate (Q) from about 0.45 milliliters per second (mL/sec) to about 0.84 mL/sec. In this example, the flow rate (Q) is increased substantially (e.g. about 86%) with only a small increase (e.g. greater by about 16%) in the diameter of the single larger distal lumen relative to the effective combined diameters of the smaller lumens preferably without increasing the corresponding outer diameter of the catheter shaft such that the blood vessel will not be occluded by the catheter. The catheter may be easily removed by the interventionalist by pulling it out from the patients' body.

Referring to FIGS. 1A-1D, a catheter in accordance with at least one embodiment of the present invention is provided. The catheter 10 is configured to be inserted into a patients' body and has an elongated shaft 12 with a proximal portion 14 extending to a distal portion 16. The elongated shaft 12 is made from polymeric material which is preferably compliant and kink resistant, e.g., soft an elastomeric. In one example, the entire elongated shaft 12 is made from a polymeric material or resin e.g., by an extrusion process, pultrusion process or the alike. In another example, the elongated shaft 12 is made from at least two polymeric materials or resins, e.g., by co-extrusion, two-shot molding or the alike. For example, the elongated shaft 12 may be co-extruded from two different polymeric resins where the first polymeric resin is extruded to form an inner layer and the second polymeric material is extruded to form an outer layer of the elongated shaft 12.

The proximal portion 14 of the elongated shaft 12 has a plurality of first lumens 18, 20 and 22 that are formed through the proximal portion 14. As illustrated, the three first lumens 18, 20 and 22 are separated from each other in a non-coaxial relationship by two septums 24 and 26. One septum 24 has two opposing arcuate surfaces 2 and 4 that correspondingly form part of the circular shapes of the two first lumens 18 and 20. The other septum 26 has two adjacent arcuate surfaces 6 and 8 and an opposing flat surface 9 that form part of the circular shapes of the two first lumens 18 and 20 and the flat portion of the other first lumen 22, respectively. Other septums with a variety of different shaped surfaces and correspondingly different shaped first lumens may be also be used.

The first lumens 18, 20 and 22 have a combined flow area (A) for providing treatment through the proximal portion 14. In particular, the combined flow area A is the sum of the flow areas 28, 30 and 32 of each of the first lumens 18, 20 and 22, respectively. The flow area 28 of the first lumen 18 is defined by $\pi(d/2)^2$, the flow area 30 of first lumen 20 is defined by $\pi(d'/2)^2$, and the flow area of first lumen 22 is defined by $\frac{1}{2} \pi(R)^2$. Accordingly in this example, the combined flow area of the first lumens 18, 20 and 22 is defined as $A = \frac{1}{4} \pi(d^2 + d'^2 + 2R^2)$.

The distal portion 16 has a second lumen 34 in fluid communication with the first lumens 18, 20 and 22. In at least one embodiment, the septums 24 and 26 terminate at some point distally along the proximal portion 14 to merge the first lumens 18, 20 and 22 with the second lumen 34.

As illustrated in FIGS. 1B-1D, the elongated shaft 12 has a longitudinal axis 36 and the septums 24 and 26 have cross sections that are uniformly extruded along a length of the longitudinal axis 36 to define the septums 24 and 26. The septums 24 and 26 terminate abruptly at position along the longitudinal axis 36 to merge the first lumens 18, 20 and 22 into the second lumen 34. In an alternative embodiment illustrated in FIG. 1E, the septums 24 and/or 26 may have a variable width 38 that tappers distally along a length of the longitudinal axis 36, terminating the septums 24 and/or 26 at some point distally along the proximal portion 14.

It is believed that the shorter the length that the septums 24 and 26 extend within the elongated shaft 12, the more the volumetric flow provided by the catheter 10 will be improved. In one example, the elongated shaft 12 has a length of at least about 15 cm and the septums 24 and 26 extend in the elongated shaft 12 for a length not exceeding about 10 cm. In a preferred example, the septums 24 and 26 extend in the elongated shaft 12 for a length not exceeding about 3 cm.

As illustrated in FIG. 1C, the second lumen 34 has a diameter (2R' which is double the radius (R')) and a second flow area 40. The second flow area 40 is defined by $\pi R'^2$. The second flow area 40 is greater than the combined flow area A of the first lumens 18, 20 and 22 by preferably at least the cross-sectional area of the septums 24 and 26 to enhance fluidly communicating treatment to the patient. In an alternative embodiment, the second flow area 40 is greater than the associated flow area for any one of the first lumens 18, 20 and 22.

The proximal and distal portions 14 and 16 of the elongated shaft 12 have corresponding outer diameters 42 and 44. In one embodiment, the outer diameter 44 of the distal portion 16 substantially matches the other diameter 42 of the proximal portion 14. In another embodiment, the outer diameters 42 and 44 of the elongated shaft 12 are between about 4 and 10 French.

Figure 1A:
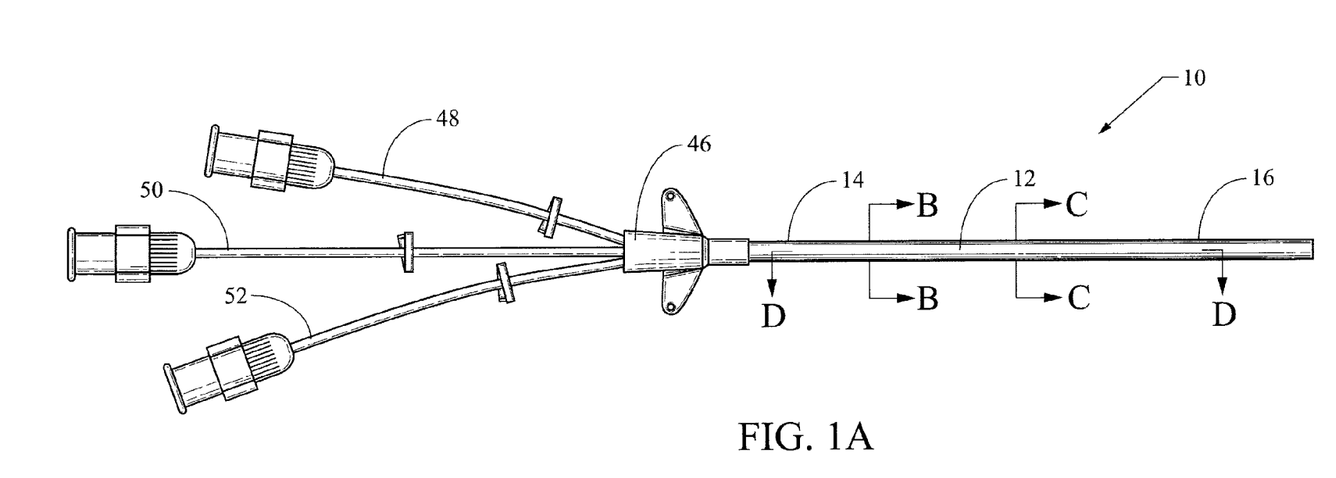
FIG. 1A is a side view of a catheter in accordance with an embodiment of the present invention.
Figure 1B:
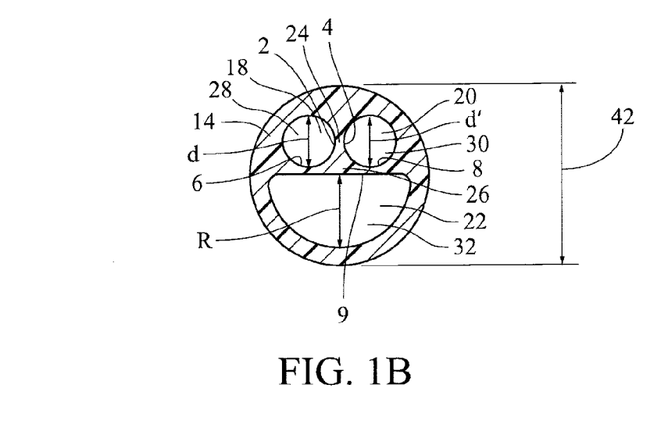
FIG. 1B is an axial cross-section of the catheter depicted in FIG. 1A.
Figure 1C:
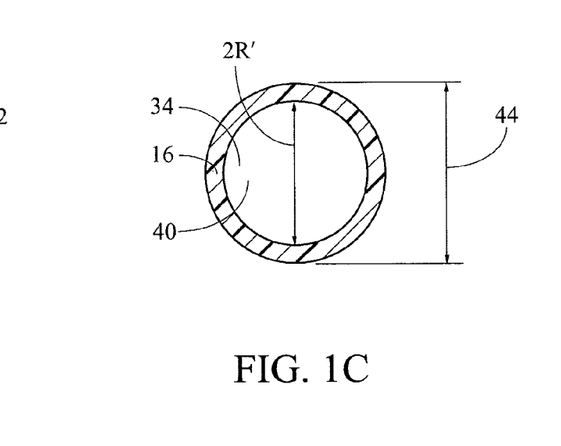
FIG. 1C is another axial cross-section of the catheter depicted in FIG. 1A.
Figure 1D:
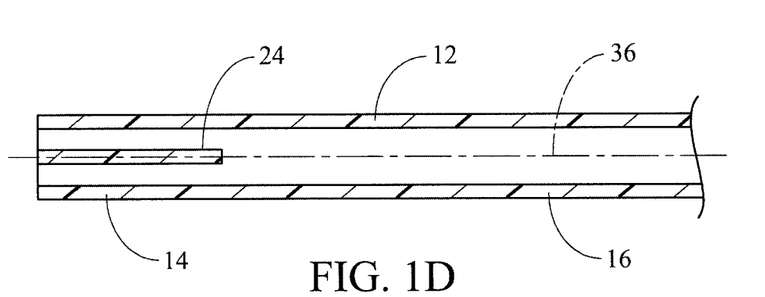
FIG. 1D is a longitudinal cross-section of the catheter depicted in FIG. 1A in accordance with one embodiment of the present invention.
Figure 1E:
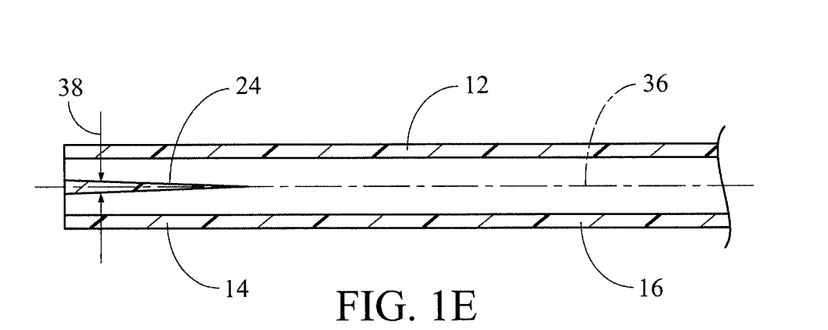
FIG. 1E is a longitudinal cross-section of the catheter depicted in FIG. 1A in accordance with another embodiment of the present invention.

As illustrated in FIG. 1A, the catheter 10 further comprises a manifold hub 46 which is attached to a proximal end of the proximal portion 14 of the elongated shaft 12. The manifold hub 46 may be formed of molded plastic or any other suitable material and/or process known to those skilled in the art and is configured to fluidly communicate with each of the first lumens 18, 20 and 22.

A plurality of three extension tubes 48, 50 and 52 are connected the manifold hub 46 and extend proximally therefrom. Each of the extension tubes 48, 50 and 52 are configured to receive a respective therapeutic fluid and to communicate the fluids to the manifold hub 46 for delivery to each of the first lumen 18, 20 and 22.

Figure 4:
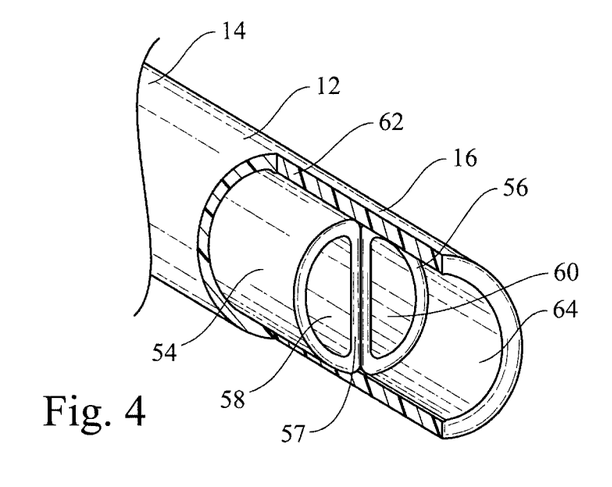
FIG. 4 is a tear-away perspective view of a catheter shaft in accordance with one embodiment of the present invention.

Referring to FIG. 4 is one embodiment of an alternative construction for the elongated shaft 12 of the catheter 10. The elongated shaft 12 includes two inner tubes 54 and 56 preferably formed of plastic material and having first lumens 58 and 60 formed therethrough, respectively. As illustrated, the inner tubes 54 and 56 each have a "D" shaped cross-sectional profile which is extruded longitudinally to form the inner tubes 54 and 56. The inner tubes 54 and 56 are positioned adjacent to each other such that their flat surfaces are immediately adjacent one another to form the septum 57. Accordingly, the septum 57 has two substantially flat opposing surfaces that are correspondingly formed along the first lumens 58 and 60. An outer tube 62, which is preferably formed of extruded plastic, is disposed about the inner tubes 54 and 56 and extends distally from the inner tubes 54 and 56 to form the distal portion 16 of the elongated shaft and to define the second lumen 64.

Figure 2A:
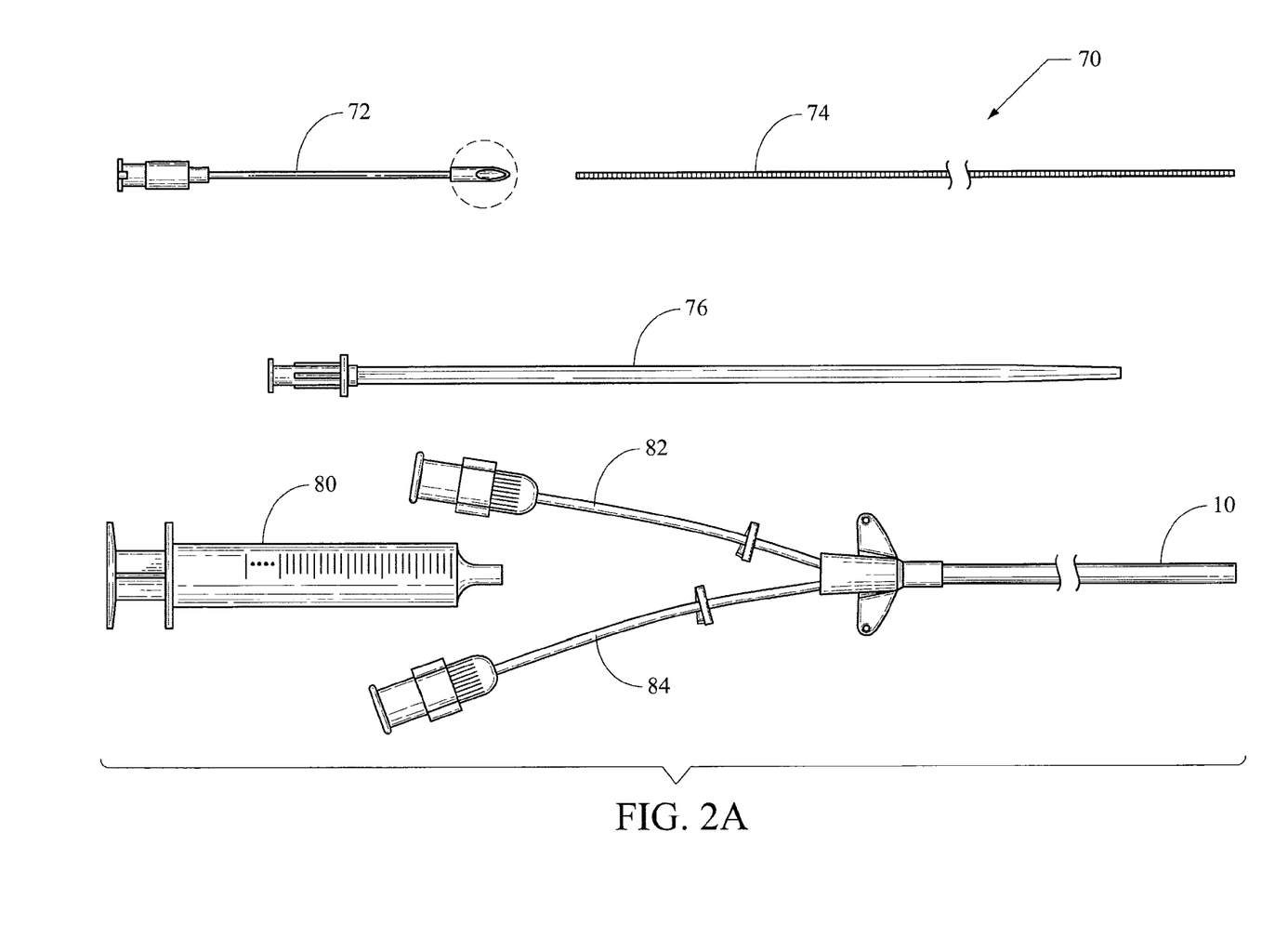
FIG. 2A is an exploded view of a catheterization kit in accordance with an embodiment of the present invention.
Figure 2B:
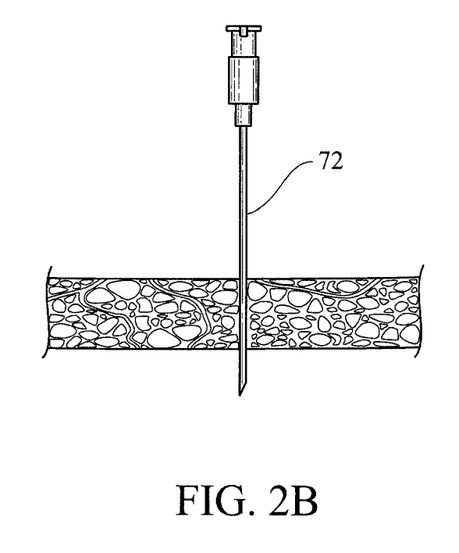
FIG. 2B is a side view of a needle inserted into a patient's body in accordance with one embodiment of the present invention.
Figure 2C:
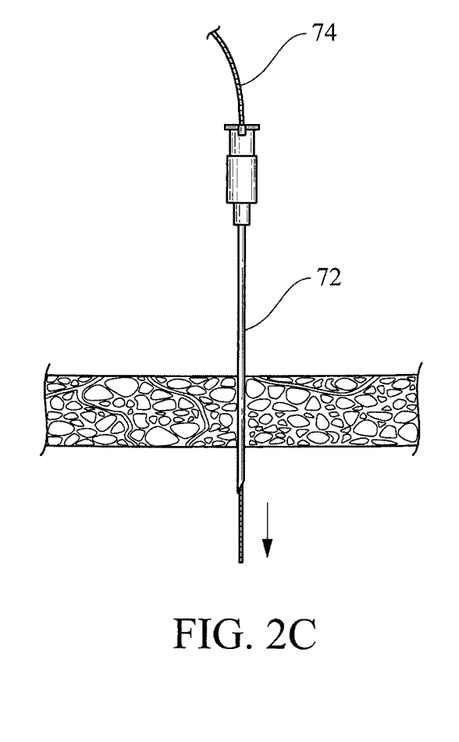
FIG. 2C is a side view of a wire guide being introduced into a patient's body in accordance with an embodiment of the present invention.
Figure 2D:
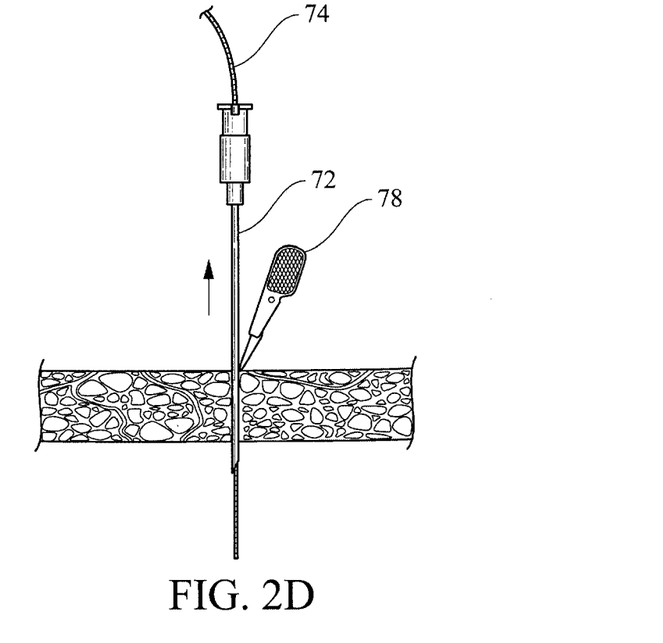
FIG. 2D is side view of an example of an entry point into a patient's body being expanded in accordance with one embodiment of the present invention.

Referring to FIGS. 2A-2F, at least one embodiment of a catheterization kit is provided. As illustrated in FIG. 2A, the kit 70 includes a needle 72, a wire guide 74 and the catheter 10 as discussed in the foregoing paragraphs. The needle 72 is for percutaneously introducing the wire guide 74 into the patients' body (see FIGS. 2B-2C) through an access site and the wire guide 74 is for providing the catheter 10 a path for insertion into the patients' body (see FIG. 2F), such as for example, using the well-known Seldinger technique. A cutting device 78 may also be used to expand the access site (see FIG. 2D).

Figure 2E:
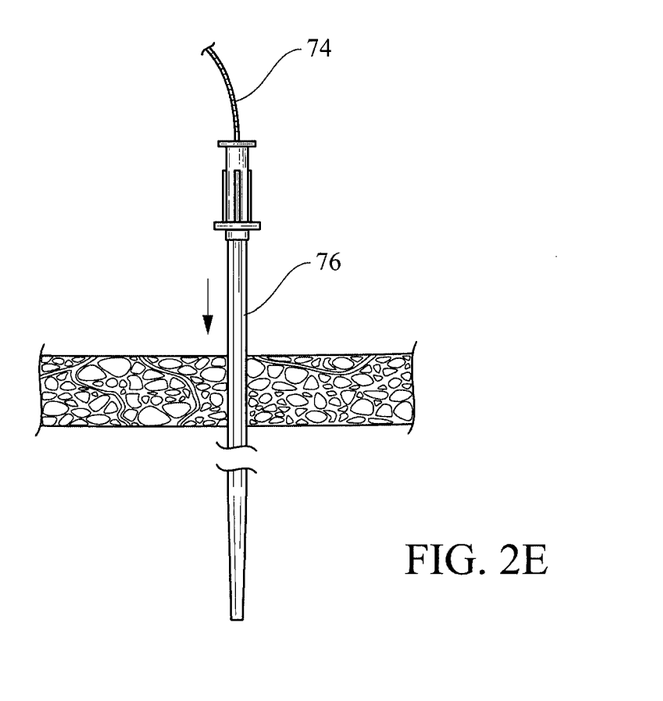
FIG. 2E is a side view of a dilator being introduced into a patient's body in accordance with one embodiment of the present invention.

The kit 70 may also include a dilator 76 configured to be advanced over the wire guide 74. The dilator 76 is used for dilating at least a portion of the path to facilitate inserting the catheter 10 into the patients' body (see FIGS. 2A and 2E-2F). At least one syringe 80 may be part of the kit 70 for containing and administering various treatments and is configured to interface with the proximal end of at least one of the extension tubes 82 and 84 of the catheter 10 for fluidly communication the treatment with at least one of the first lumens 18, 20 or 22.

Figures 2F, 3:
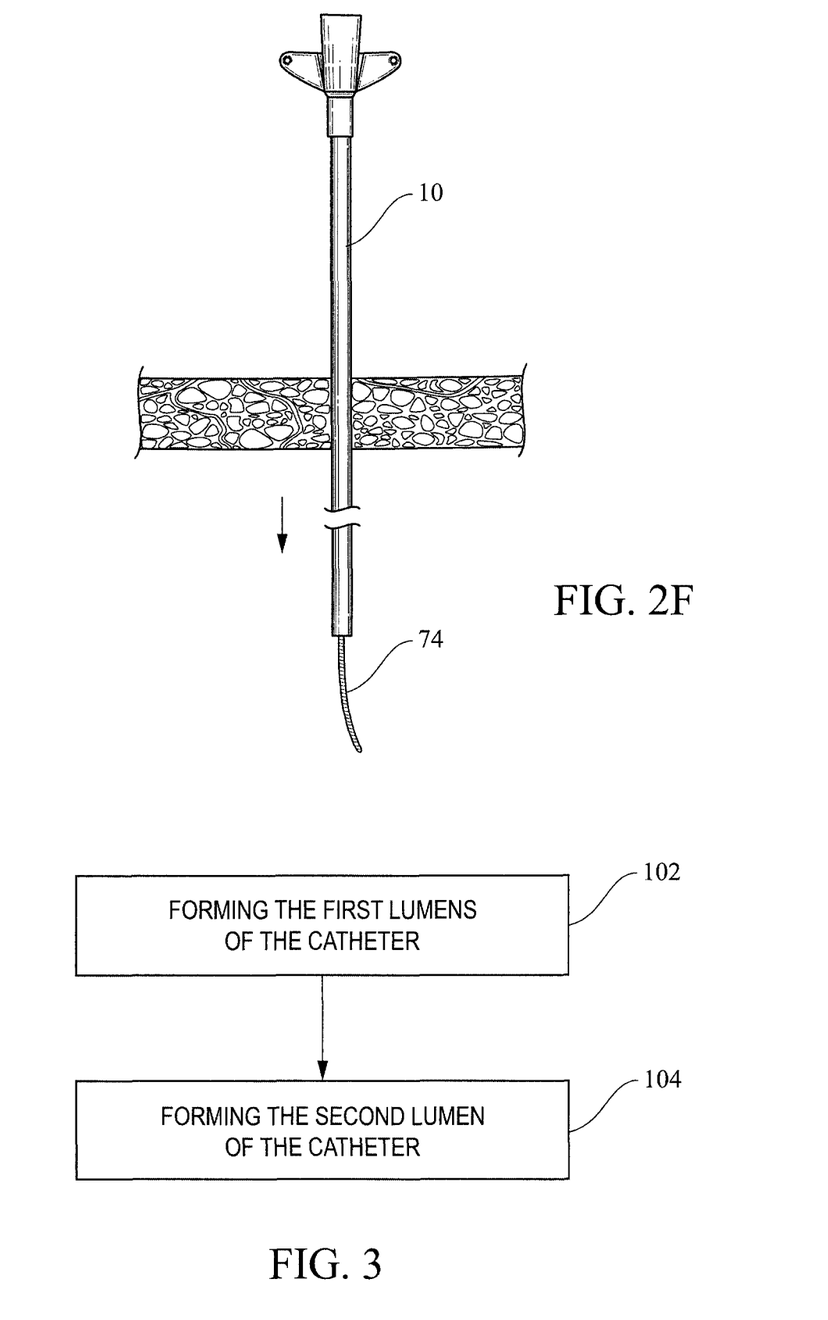
FIG. 2F is a side view of a catheter being introduced into a patient's body in accordance with an embodiment of the present invention.
FIG. 3 is a flow chart of a method for making a catheter in accordance with one example of the present invention.
Figure 5:
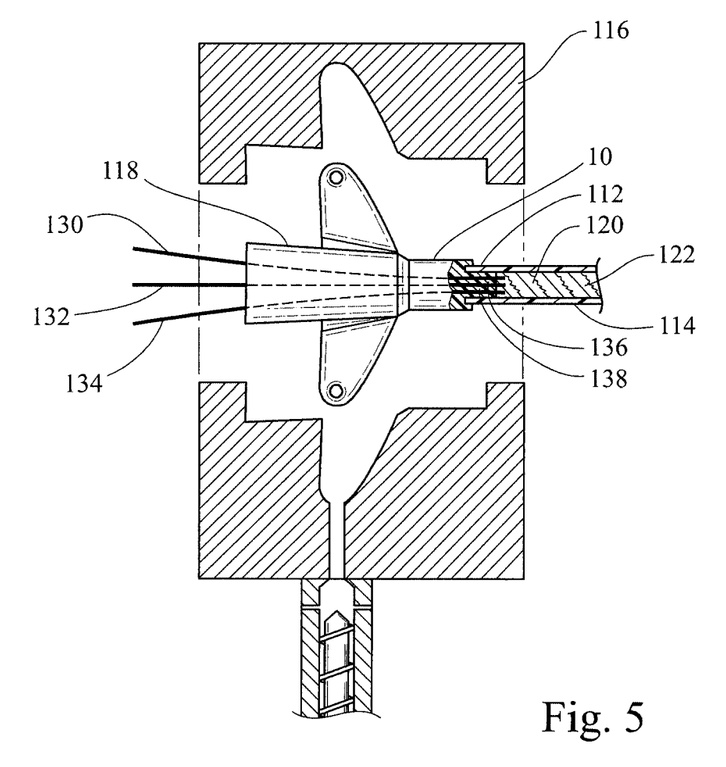
FIG. 5 is a partial cross-sectional view of one example of a catheter being formed in accordance with the present invention.

Referring to FIGS. 3 and 5, a method for making a catheter in accordance with one example of the present invention is provided. The method comprises forming a plurality of first lumens through a proximal portion of the catheter at 102 including forming at least one septum separating the first lumens in non-coaxial relationship with each other. As illustrated in FIG. 5, plastic material is overmolded onto a proximal end of the proximal portion 112 of the catheter's extruded plastic shaft 114 in a mold 116 to form a manifold hub 118. The shaft 114 contains a removable support core 120 that is spaced apart from the proximal end of the shaft 114. The support core 120 is for maintaining the shape of the shaft 114 during the insert molding process and for providing a molding shut-off for preventing the lumen 122 of the shaft 114 from filling with the plastic material.

Three non-coaxial core wires 130, 132 and 134 extend proximally from the support core 120 and are overmolded with the plastic material that forms the manifold hub 118 and which partly fills the shaft lumen 122 up to the support core to form the septums 136 and 138. Accordingly, the septums 136 and 138 terminate at the interface with the support core 120 within the shaft lumen 122. The three core wires 130, 132 and 134 are removed from both the manifold hub 118 and the support core 120 to provide corresponding first lumens that extend through the proximal portion 112 and the manifold hub 118. The first lumens have a combined flow area for advancing a treatment through the proximal portion 112 of the shaft 114.

A second lumen is formed through the distal portion of the catheter at 104 including the at least one septum terminating distally in the proximal portion of the shaft to merge the first lumens with the second lumen. In particular, the support core 120 is removed from the shaft lumen 122 and the portion of the shaft lumen 122 extending distally from the point of termination of the septums 136 and 138 defines the second lumen. The second lumen has a second flow area that is greater than the combined flow area of the first lumens for advancing the treatment to a patient. Other suitable methods and processes may also be used for forming the multi-lumen catheter in accordance with the present invention.

As a person skilled in the art will readily appreciate, the above description is meant as an illustration of the implementation of the principles of the invention. This description is not intended to limit the scope or application of this invention in that the invention is susceptible to modification, variation, and change, without departing from the spirit of this invention as defined in the following claims.

What we claim is:

1. A catheter for insertion into a patient's body for providing treatment thereto, the catheter comprising:
    an elongated shaft having a proximal portion extending to a distal portion, the proximal portion having:
    a plurality of first lumens formed therethrough and at least one septum separating the first lumens in non-coaxial relationship with each other, the first lumens each having an associated flow area for providing the treatment through the proximal portion, the distal portion having a second lumen in fluid communication with the first lumens, the septum terminating distally in the proximal portion to merge the first lumens with the second lumen, the second lumen having a second flow area that is greater than any one of the associated flow areas of the first lumens for providing the treatment to the patient;
    a manifold hub attached to a proximal end of the proximal portion of the elongated shaft; and
    a plurality of extension tubes extending proximally from the manifold hub, each of the extension tubes cooperatively configured with the manifold hub to fluidly communicate at least a portion of the treatment to one of the first lumens, each extension tube having an external surface that is not fixedly attached to any other external surface of any other extension tube.

2. The catheter according to claim 1 wherein the proximal and distal portions each have an outer diameter, the outer diameter of the proximal portion substantially matching the outer diameter of the distal portion.

3. The catheter according to claim 1 wherein the proximal and distal portions each have an outer diameter that is between about 4 and 10 French.

4. The catheter according to claim 1 wherein the elongated shaft has a length of at least about 15 centimeters and the septum extends in the elongated shaft for a length not exceeding about 10 centimeters.

5. The catheter according to claim 1 wherein the elongated shaft has a longitudinal axis and the septum has a variable width that tapers distally along a length of the longitudinal axis.

6. The catheter according to claim 1 wherein the elongated shaft has a longitudinal axis and the septum has a cross section that is uniformly extruded along a length of the longitudinal axis to define the septum, the septum terminating abruptly about a position along the longitudinal axis to merge the first lumens into the second lumen.

7. The catheter according to claim 1 wherein the elongated shaft includes:
    a plurality of inner tubes correspondingly defining the first lumens; and
    an outer tube disposed about the inner tubes and extending distally therefrom defining the second lumen.

8. The catheter according to claim 7 wherein at least two of the inner tubes are positioned adjacent to each other and are configured to form the septum with a substantially flat surface formed along each of the corresponding first lumens.

9. A catheterization kit comprising:
    a catheter for insertion into a patient's body for providing treatment thereto, the catheter including:
        an elongated shaft having a proximal portion extending to a distal portion, the proximal portion having a plurality of first lumens formed therethrough and at least one septum separating the first lumens in non-coaxial relationship with each other, the first lumens each having an associated flow area for providing the treatment through the proximal portion, the distal portion having a second lumen in fluid communication with the first lumens, the septum terminating distally in the proximal portion to merge the first lumens with the second lumen, the second lumen having a second flow area that is greater than any one of the associated flow areas of the first lumens for providing the treatment to the patient;
        a manifold hub attached to a proximal end of the proximal portion of the elongated shaft; and
        a plurality of extension tubes extending proximally from the manifold hub, each of the extension tubes cooperatively configured with the manifold hub to fluidly communicate at least a portion of the treatment to one of the first lumens, each extension tube having an external surface that is not fixedly attached to any other external surface of any other extension tube;
    a wire guide for providing the catheter a path during insertion into the patient's body; and
    a needle for introducing the wire guide into the patient's body.

10. The kit according to claim 9 further comprising a dilator configured to be advanced over the wire guide for dilating at least a portion of the path to facilitate inserting the catheter into the patient's body.

11. The kit according to claim 9 further comprising at least one syringe configured for fluid communication with at least one of the first lumens for delivering at least a portion of the treatment to the at least one of the first lumens.

12. The kit according to claim 9 wherein the proximal and distal portions each have an outer diameter, the outer diameter of the proximal portion substantially matching the outer diameter of the distal portion.

13. The kit according to claim 10 wherein the elongated shaft includes:
    a plurality of inner tubes correspondingly defining the first lumens; and
    an outer tube disposed about the inner tubes and extending distally therefrom defining the second lumen.

14. The kit according to claim 9 wherein the elongated shaft has a longitudinal axis and the septum has a variable width that tapers distally along a length of the longitudinal axis.

15. The kit according to claim 9 wherein the elongated shaft has a longitudinal axis and the septum has a cross section that is uniformly extruded along a length of the longitudinal axis to define the septum, the septum terminating abruptly about a position along the longitudinal axis to merge the first lumens into the second lumen.

* * * * *